United States Patent [19]

Stavrianopoulos et al.

[11] Patent Number: 4,994,373
[45] Date of Patent: Feb. 19, 1991

[54] METHOD AND STRUCTURES EMPLOYING CHEMICALLY-LABELLED POLYNUCLEOTIDE PROBES

[75] Inventors: Jannis G. Stavrianopoulos, New York; Dollie Kirtikar, Elmhurst; Kenneth H. Johnston; Barbara E. Thalenfeld, both of New York, all of N.Y.

[73] Assignee: Enzo Biochem, Inc., New York, N.Y.

[21] Appl. No.: 385,986

[22] Filed: Jul. 20, 1989

Related U.S. Application Data

[63] Continuation of Ser. No. 732,374, May 9, 1985, abandoned, which is a continuation-in-part of Ser. No. 461,469, Jan. 21, 1983, abandoned.

[51] Int. Cl.[5] .................... C12Q 1/68; C07H 21/00; G01N 33/533
[52] U.S. Cl. ........................................... 435/6; 435/7; 435/188; 435/296; 435/300; 435/4; 435/810; 436/94; 436/501; 436/524; 436/527; 436/531; 436/532; 436/800; 436/810; 526/27; 935/77; 935/78; 935/86; 935/87
[58] Field of Search ................. 536/27; 436/800, 810; 935/77, 78, 86, 87

[56] References Cited

U.S. PATENT DOCUMENTS

| | | | |
|---|---|---|---|
| 3,652,761 | 3/1972 | Weetall | 435/7 X |
| 4,358,535 | 11/1982 | Falkow et al. | 435/6 X |
| 4,391,904 | 7/1983 | Litman et al. | 435/7 |
| 4,483,920 | 11/1984 | Gillespie et al. | 435/6 |
| 4,581,333 | 4/1986 | Kourilsky et al. | 435/6 |

Primary Examiner—Robert A. Wax
Assistant Examiner—Ardin H. Marschel
Attorney, Agent, or Firm—Serle I. Mosoff; Elaine P. Brenner; Helen Tzagoloff

[57] ABSTRACT

Polynucleotide sequences in a sample of biological or nonbiological material are detected by a method involving fixing of the sequences on a solid support and forming an entity between the fixed sequences and chemically-labeled polynucleotide or oligonucleotide probes having a sequence complementary to the fixed sequence for determining the identification and/or presence of the target polynucleotide sequences. The chemical label covalently or noncovalently attached to the probe comprises a signalling moiety capable of generating a soluble signal detectable by spectrophotometric assay techniques.

27 Claims, No Drawings

METHOD AND STRUCTURES EMPLOYING CHEMICALLY-LABELLED POLYNUCLEOTIDE PROBES

This is a continuation of applicants' U.S. patent application Ser. No. 06/732,374, filed May 9, 1985, now abandoned, which is a continuation-in-part of applicants' U.S. patent application Ser. No. 06/461,469, filed Jan. 21, 1983, now abandoned.

TECHNICAL FIELD OF INVENTION

The present invention relates generally to the detection of genetic material by polynucleotide probes. More specifically, it relates to a method for quantifiably detecting a targeted polynucleotide sequence in a sample of biological and/or nonbiological material employing a probe capable of generating a soluble signal. The method and products disclosed herein in accordance with the invention are expected to be adaptable for use in many laboratory, industrial, and medical applications wherein quantifiable and efficient detection of genetic material is desired.

BACKGROUND OF THE INVENTION

In the description, the following terms are employed:

Analyte—A substance or substances, either alone or in admixtures, whose presence is to be detected and, if desired, quantitated. The analyte may be a DNA or RNA molecule of small or high molecular weight, a molecular complex including those molecules, or a biological system containing nucleic acids, such as a virus, a cell, or group of cells. Among the common analytes are nucleic acids (DNA and RNA) or segments thereof, oligonucleotides, either single- or double-stranded, viruses, bacteria, cells in culture, and the like. Bacteria, either whole or fragments thereof, including both gram positive and gram negative bacteria, fungi, algae, and other microorganisms are also analytes, as well as animal (e.g., mammalian) and plant cells and tissues.

Probe—A labelled polynucleotide or oligonucleotide sequence which is complementary to a polynucleotide or oligonucleotide sequence of a particular analyte and which hybridizes to said analyte sequence.

Label—That moiety attached to a polynucleotide or oligonucleotide sequence which comprises a signalling moiety capable of generating a signal for detection of the hybridized probe and analyte. The label may consist only of a signalling moiety, e.g., an enzyme attached directly to the sequence. Alternatively, the label may be a combination of a covalently attached bridging moiety and signalling moiety or a combination of a non-covalently bound bridging moiety and signalling moiety which gives rise to a signal which is detectable, and in some cases quantifiable.

Bridging Moiety—That portion of a label which on covalent attachment or non-covalent binding to a polynucleotide or oligonucleotide sequence acts as a link or a bridge between that sequence and a signalling moiety.

Signalling Moiety—That portion of a label which on covalent attachment or non-covalent binding to a polynucleotide or oligonucleotide sequence or to a bridging moiety attached or bound to that sequence provides a signal for detection of the label.

Signal—That characteristic of a label or signalling moiety that permits it to be detected from sequences that do not carry the label or signalling moiety.

The analysis and detection of minute quantities of substances in biological and non-biological samples has become a routine practice in clinical, diagnostic and analytical laboratories. These detection techniques can be divided into two major classes: (1) those based on ligand-receptor interactions (e.g., immunoassay-based techniques), and (2) those based on nucleic acid hybridization (polynucleotide sequence-based techniques).

Immunoassay-based techniques are characterized by a sequence of steps comprising the noncovalent binding of an antibody and antigen complementary to it. See, for example, T. Chard, *An Introduction To Radioimmunoassay And Related Techniques* (1978).

Polynucleotide sequence-based detection techniques are characterized by a sequence of steps comprising the non-covalent binding of a labelled polynucleotide sequence or probe to a complementary sequence of the analyte under hybridization conditions in accordance with the Watson-Crick base pairing of adenine (A) and thymine (T), and guanine (G) and cytosine (C), and the detection of that hybridization. [M. Grunstein and D. S. Hogness, "Colony Hybridization: A Method For The Isolation Of Cloned DNAs That Contain A Specific Gene", *Proc. Natl. Acad. Sci. U.S.A.*, 72, pp. 3961–65 (1975)]. Such polynucleotide detection techniques can involve a fixed analyte [see, e.g., U.S. Pat. No. 4,358,535 to Falkow et al], or can involve detection of an analyte in solution [see U.K. patent application No. 2,019,408 A].

The primary recognition event of polynucleotide sequence-based detection techniques is the non-covalent binding of a probe to a complementary sequence of an analyte, brought about by a precise molecular alignment and interaction of complementary nucleotides of the probe and analyte. This binding event is energetically favored by the release of non-covalent bonding free energy, e.g., hydrogen bonding, stacking free energy and the like.

In addition to the primary recognition event, it is also necessary to detect when binding takes place between the labelled polynucleotide sequence and the complementary sequence of the analyte. This detection is effected through a signalling step or event. A signalling step or event allows detection in some quantitative or qualitative manner, e.g., a human or instrument detection system, of the occurrence of the primary recognition event.

The primary recognition event and the signalling event of polynucleotide sequence based detection techniques may be coupled either directly or indirectly, proportionately or inversely proportionately. Thus, in such systems as nucleic acid hybridizations with sufficient quantities of radiolabeled probes, the amount of radio-activity is usually directly proportional to the amount of analyte present. Inversely proportional techniques include, for example, competitive immunoassays, wherein the amount of detected signal decreases with the greater amount of analyte that is present in the sample.

Amplification techniques are also employed for enhancing detection wherein the signalling event is related to the primary recognition event in a ratio greater than 1:1. For example, the signalling component of the assay may be present in a ratio of 10:1 to each recognition component, thereby providing a 10-fold increase in sensitivity.

A wide variety of signalling events may be employed to detect the occurrence of the primary recognition event. The signalling event chosen depends on the particular signal that characterizes the label or signalling moiety of the polynucleotide sequence employed in the primary recognition event. Although the label may only consist of a signalling moiety, which may be detectable, it is more usual for the label to comprise a combination of a bridging moiety covalently or non-covalently bound to the polynucleotide sequence and a signalling moiety that is itself detectable or that becomes detectable after further modification.

The combination of bridging moiety and signalling moiety, described above, may be constructed before attachment or binding to the sequence, or it may be sequentially attached or bound to the sequence. For example, the bridging moiety may be first bound or attached to the sequence and then the signalling moiety combined with that bridging moiety. In addition, several bridging moieties and/or signalling moieties may be employed together in any one combination of bridging moiety and signalling moiety.

Covalent attachment of a signalling moiety or bridging moiety/signalling moiety combination to a sequence is exemplified by the chemical modification of the sequence with labels comprising radioactive moieties, fluorescent moieties or other moieties that themselves provide signals to available detection means or the chemical modification of the sequence with at least one combination of bridging moiety and signalling moiety to provide that signal.

Non-covalent binding of a signalling moiety or bridging moiety/signalling moiety to a sequence involve the non-covalent binding to the sequence of a signalling moiety that itself can be detected by appropriate means, i.e., or enzyme, or the non-covalent binding to the sequence of a bridging moiety/signalling moiety to provide a signal that may be detected by one of those means. For example, the label of the polynucleotide sequence may be a bridging moiety non-covalently bound to an antibody, a fluorescent moiety or another moiety which is detectable by appropriate means. Alternatively, the bridging moiety could be a lectin, to which is bound another moiety that is detectable by appropriate means.

There are a wide variety of signalling moieties and bridging moieties that may be employed in labels for covalent attachment or non-covalent binding to polynucleotide sequences useful as probes in analyte detection systems. They include both a wide variety of radioactive and non-radioactive signalling moieties and a wide variety of non-radioactive bridging moieties. All that is required is that the signalling moiety provide a signal that may be detected by appropriate means and that the bridging moiety, if any, be characterized by the ability to attach covalently or to bind non-covalently to the sequence and also the ability to combine with a signalling moiety.

Radioactive signalling moieties and combinations of various bridging moieties and radioactive signalling moieties are characterized by one or more radioisotopes such as $^{32}P$, $^{131}I$, $^{14}C$, $^{3}H$, $^{60}Co$, $^{59}Ni$, $^{63}Ni$ and the like. Preferably, the isotope employed emits $\beta$ or $\gamma$ radiation and has a long half life. Detection of the radioactive signal is then, most usually, accomplished by means of a radioactivity detector, such as exposure to a film.

The disadvantages of employing a radioactive signalling moiety on a probe for use in the identification of analytes are well known to those skilled in the art and include the precautions and hazards involved in handling radioactive material, the short life span of such material and the correlatively large expenses involved in use of radioactive materials.

Non-radioactive signalling moieties and combinations of bridging moieties and non-radioactive signalling moieties are being increasingly used both in research and clinical settings. Because these signalling and bridging moieties do not involve radioactivity, the techniques and labelled probes using them are safer, cleaner, generally more stable when stored, and consequently cheaper to use. Detection sensitivities of the non-radioactive signalling moieties also are as high or higher than radiolabelling techniques.

Among the presently preferred non-radioactive signalling moieties or combinations of bridging/signalling moieties useful as non-radioactive labels are those based on the biotin/avidin binding system. [P. R. Langer et al., "Enzymatic Synthesis Of Biotin-Labeled Polynucleotides: Novel Nucleic Acid Affinity Probes", *Proc. Natl. Acad. Sci. U.S.A.*, 78, pp. 6633-37 (1981); J. Stavrianopoulos et al., "Glycosylated DNA Probes For Hybridization/Dection Of Homologous Sequences", presented at the Third Annual Congress For Recombinant DNA Research (1983); R. H. Singer and D. C. Ward, "Actin Gene Expression Visualized In Chicken Muscle Tissue Culture By Using In Situ Hybridization With A Biotinated Nucleotide Analog", *Proc. Natl. Acad. Sci. U.S.A.*, 79, pp. 7331-35 (1982)]. For a review of non-radioactive signalling and bridging/signalling systems, both biotin/avidin and otherwise, see D. C. Ward et al., "Modified Nucleotides And Methods Of Preparing And Using Same", European Patent application No. 63879.

Generally, the signalling moieties employed in both radioactive and non-radioactive detection techniques involve the use of complex methods for determining the signalling event, and/or supply only an unquantitable positive or negative response. For example, radioactive isotopes must be read by a radioactivity counter; while signalling moieties forming insoluble "signals", i.e., precipitates, certain fluorescers, and the like [see, e.g., David et al., U.S. Pat. No. 4,376,100] only provide detection not quantitation of the analyte present in the tested sample.

One step toward facilitating rapid and efficient quantitation as well as detection of the hybridization event was the work of Heller et al. in European Patent Application Nos. 70685 and 70687 which describe the use of a signalling moiety which produces a soluble signal for measurable detection by a spectrophotometer. These European patent applications disclose the use of two different probes complementary to different portions of a gene sequence, with each probe being labelled at the end which will abut the other probe upon hybridization. The first probe is labelled with a chemiluminescent complex that emits lights of a specific wavelength. The second probe is labelled with a molecule that emits light of a different wavelength measurable by spectrophotometry when excited by the proximity of the first signalling moiety. However, this technique is performed in solution and can generate false positive results in the absence of the analyte if the two probes happen to approach too closely in solution and react with each other.

Similarly, U.K. Patent Application Ser. No. 2,019,408A, published Oct. 31, 1979, discloses a method for detecting nucleic acid sequences in solution by employing an enzyme-labelled RNA or DNA probe which, upon contact with a chromogen substrate, provides an optically readable signal. The analytes may be separated from contaminants prior to hybridization with the probe, or, alternatively, the hybrid probe-analyte may be removed from solution by conventional means, i.e., centrifugation, molecular weight exclusion, and the like. Like Heller's technique, this method is performed in solution.

There remains therefore a need in the art for a reliable, simple and quantifiable technique for the detection of analytes of interest in biological and non-biological samples.

SUMMARY OF THE INVENTION

The invention provides a solution for the disadvantages of presently available methods of detecting analytes by a novel combination of hybridization and immunological techniques. In the present invention, chemically labelled polynucleotide or oligonucleotide probes are employed to detect analytes by having the capacity to generate a reliable, easily quantifiable soluble signal.

Analytes to be detected by the detection processes of this invention may be present in any biological or non-biological sample, such as clinical samples, for example, blood urine, feces, saliva, pus, semen, serum, other tissue samples, fermentation broths, culture media, and the like. If necessary, the analyte may be pre-extracted or purified by known methods to concentrate its nucleic acids. Such nucleic acid concentration procedures include, for example, phenol extraction, treatment with chloroform-isoamyl alcohol or chloroform-octanol, column chromatography (e.g., Sephadex, hydroxyl apatite), and CsCl equilibrium centrifugation. The analyte, separated from contaminating materials, if present, is according to the present invention, fixed in hybridizable form to a solid support.

Analytes in a biological sample are preferably denatured into single-stranded form, and then directly fixed to a suitable solid support. Alternatively, the analyte may be directly fixed to the support in double-stranded form, and then denatured. The present invention also encompasses indirect fixation of the analyte, such as in situ techniques where the cell is fixed to the support and sandwich hybridization techniques where the analyte is hybridized to a polynucleotide sequence that is fixed to the solid support. It is preferred that the solid support to which the analyte is fixed be non-porous and transparent, such as glass, or alternatively, plastic, polystyrene, polyethylene, dextran, polypropylene and the like. Conventional porous materials, e.g., nitrocellulose filters, although less desirable for practice of the method of the present invention, may also be employed as a support.

It is also highly desirable that the analyte be easily fixed to the solid support. The capability to easily fix the analyte to a transparent substrate would permit rapid testing of numerous samples by the detection techniques described herein.

Chemically-labeled probes are then brought into contact with the fixed single-stranded analytes under hybridizing conditions. The probe is characterized by having covalently attached to it a chemical label which consists of a signalling moiety capable of generating a soluble signal. Desirably, the polynucleotide or oligonucleotide probe provides sufficient number of nucleotides in its sequence, e.g., at least about 25, to allow stable hybridization with the complementary nucleotides of the analyte. The hybridization of the probe to the single-stranded analyte with the resulting formation of a double-stranded or duplex hybrid is then detectable by means of the signalling moiety of the chemical label which is attached to the probe portion of the resulting hybrid. Generation of the soluble signal provides simple and rapid visual detection of the presence of the analyte and also provides a quantifiable report of the relative amount of analyte present, as measured by a spectrophotometer or the like.

The method of the present invention involving the colorimetric or photometric determination of the hybridized probes employs as the signalling moiety reagents which are capable of generating a soluble signal, e.g., a color change in a substrate in solution. Preferable components of the signalling moiety include enzymes, chelating agents and co-enzymes, which are able to generate colored or fluorescent soluble signals. Specifically, certain chromogens upon contact with certain enzymes are utilizable in the method of the present invention. The following Table I lists exemplary components for the signalling moiety of the present invention. Each chromogen listed is reactive with the corresponding enzyme to produce a soluble signal which reports the presence of the chemically-labeled probe analyte hybrid. The superscript notation (*) indicates that the chromogen fluoresces, rather than produces a color change.

TABLE I

| ENZYME | CHROMOGEN |
| --- | --- |
| alkaline phosphatase or acid phosphatase | *4-Methylumbelliferyl phosphate |
| | *bis (4-Methylumbelliferyl phosphate |
| | 3-0-methylfluorescein. |
| | *Flavone-3-diphosphate triammonium salt |
| | p-nitrophenyl phosphate 2Na. |
| peroxidase | *Tyramine hydrochloride |
| | *3-(p-hydroxyphenyl) Propionic acid |
| | *p-Hydroxyphenethyl alcohol |
| | 2,2'-Azino-Di-3-Ethylbenzthiazoline sulfonic acid (ABTS) |
| | ortho-phenylenediamine 2HCl |
| | 0-dianisidine |
| | *5-aminosalicylic acid |
| | p-cresol |
| | 3,3'-dimethyloxybenzidine |
| | 3-methyl-2-benzothiazoline hydrazone |
| | tetramethyl benzidine |
| β-D-galactosidase | 0-nitrophenyl β-D-galactopyranoside |
| | 4-methylumbelliferyl-β-D-galactoside |
| glucose-oxidase | ABTS |

As another aspect of the present invention, the signalling moiety may be attached to the probe through the formation of a bridging entity or complex. Likely candidates for such a bridging entity would include a biotin-avidin bridge, a biotin-streptavidin bridge, or a sugar-lectin bridge.

Once the fixed probe-analyte hybrid is formed, the method may further involve washing to separate any non-hybridized probes from the area of the support.

The signalling moiety may also be attached to the probe through the bridging moiety after the washing step to preserve the materials employed. Thereafter, another washing step may be employed to separate free signalling moieties from those attached to the probe through the bridging moiety.

Broadly, the invention provides hybridization techniques which provide the same benefits as enzyme linked immunosorbent assay techniques, i.e., the qualitative and quantitative determination of hybrid formation through a soluble signal. Various techniques, depending upon the chemical label and signalling moiety of the probe, may be employed to detect the formation of the probe-analyte hybrid. It is preferred, however, to employ spectrophotometric techniques and/or colorimetric techniques for the determination of the hybrid. These techniques permit not only a prompt visual manifestation of the soluble signal generated by the signalling moiety on the double-stranded hybrid, but also permit the quantitative determination thereof, i.e., by the enzymatic generation of a soluble signal that can be quantitatively measured.

Yet another aspect of the method of the present invention involves generating the soluble signal from the probe-analyte hybrid in a device capable of transmitting light therethrough for the detection of the signal by spectrophotometric techniques. Examples of devices useful in the spectrophotometric analysis of the signal include conventional apparatus employed in diagnostic laboratories, i.e., plastic or glass wells, tubes, cuvettes or arrangements of wells, tubes or cuvettes. It may also be desirable for both the solid support to which the analyte is fixed and the device to be composed of the same material, or for the device to function as the support in addition to facilitating spectrophotometric detection.

A further aspect of the present invention provides products useful in the disclosed method for detection of a polynucleotide sequence. Among these products is a device containing a portion for retaining a fluid. Such portion contains an immobilized polynucleotide sequence hybridized to a polynucleotide or oligonucleotide probe. The probe, as described above, has covalently attached thereto a chemical label including a signalling moiety capable of generating a soluble signal. Also part of the device is a soluble signal, preferably a colored or fluorescent product, generatable by means of the signalling moiety. The portion of the device for containing the fluid is desirably a well, a tube, or a cuvette. A related product of the invention is an apparatus comprising a plurality of such devices for containing a fluid, in which at least one such device contains the above-described immobilized polynucleotide sequence, polynucleotide or oligonucleotide probe, signalling moiety, and soluble signal. Additionally the present invention provides for the novel product of a non-porous solid support to which a polynucleotide is directly fixed in hybridizable form. Such a fixed sequence may be hybridized to another polynucleotide sequence having covalently attached thereto a chemical label including a signalling moiety capable of generating a soluble signal. As indicated above, the support is preferably transparent or translucent. Such products could be advantageously employed in diagnostic kits and the like.

Other aspects and advantages of the present invention will be readily apparent upon consideration of the following detailed description of the preferred embodiments thereof.

DETAILED DESCRIPTION

The following examples are illustrative of preferred embodiments of the method of the present invention. Specifically referred to therein are methods for fixing the analyte to a non-porous solid support, as well as illustrations of the use of soluble signals in polynucleotide probes as discussed above.

EXAMPLE 1

For purposes of the present invention, an analyte is immobilized on a solid support, preferably a non-porous translucent or transparent support. To effect easy fixing of a denatured single-stranded DNA sequence to a glass support, an exemplary "fixing" procedure may involve pretreating the glass by heating or boiling for a sufficient period of time in the presence of dilute aqueous nitric acid. Approximately forty-five minutes in 5% dilute acid should be adequate to leach boron residues from a borosilicate glass surface. The treated glass is then washed or rinsed, preferably with distilled water, and dried at a temperature of about 115° C., for about 24 hours. A 10 percent solution of gamma-aminopropyltriethoxysilane, which may be prepared by dissolving the above-identified silane in distilled water followed by addition of 6N hydrochloric acid to a pH of about 3.45, will then be applied to the glass surface. The glass surface is then incubated in contact with the above-identified silane solution for about 2-3 hours at a temperature of about 45° C. The glass surface is then washed with an equal volume of water and dried overnight at a temperature of about 100° C. The resulting treated glass surface will now have available alkylamine thereon suitable for immobilizing or fixing any negatively charged polyelectrolytes applied thereto. [See Weetal, H. H. and Filbert, A. M., "Porous Glass for Affinity Chromatography Applications", *Methods in Enzymology*, Vol. XXXIV, Affinity Techniques Enzyme Purification: Part B. pp. 59–72, W. B. Jakoby and M. Wilchek, eds.]

Such treated glass could then be employed in the method of the invention. For example, glass plates provided with an array of depressions or wells would have samples of the various denatured analytes deposited therein, the single-stranded analytes being fixed to the surfaces of the wells. Thereupon, polynucleotide probes provided with a chemical label may be deposited in each of the wells for hybridization to any complementary single-stranded analyte therein. After washing to remove any non-hybridized probe, the presence of any hybrid probe-analyte is then detectable. One detection technique as described herein involves the addition of an enzyme-linked antibody or other suitable bridging entity of the label for attachment to the probe. Subsequently a suitable substrate is added to elicit the soluble signal, e.g., a color change or chemical reaction, which is then measured colorimetrically or photometrically.

EXAMPLE 2

A glass surface treated as described in Example 1 can be employed in the method of the present invention, wherein glucosylated DNA is employed as the labelled probe, and the signalling moiety comprises the combination of acid phosphatase and its substrate paranitrophenylphosphate.

In this procedure, glucosylated bacteriophage $T_4$ DNA, isolated from E. coli CR63 cultures infected with phage $T_4$ AM82 [44$^-$62$^-$] and purified to be free of chromosomal DNA, or non-glucosylated, highly purified calf thymus DNA is delivered in 100 μl portions to treated glass tubes in triplicate set. After 15-30 minutes at room temperature, the solution is removed and the tubes rinsed generously with PBS.Mg++ buffer [100 mM Na-K-PO$_4$, pH 6.5, 150 mM NaCl and 10 mM MgCl$_2$].

One set of tubes is checked for the presence of DNA by staining with ethidium bromide [100 μl of 1 mg/ml solution, 30 minutes in the dark, at room temperature]. The staining solution is removed and the tubes rinsed and checked by UV light. Both glucosylated labelled and unlabelled DNA "probe" bound to the activated glass surface by the observed red fluorescence characteristic of ethidium bromide.

To another set of tubes is delivered fluorescein-labelled ConA [100 μl of 0.1 mg/ml in PBS.Mg++ buffer]. The Concanavalin A [ConA] is obtained and solubilized in 2.0M NaCl at a concentration of 50 mg/ml, and fluorescein-labelled by reacting ConA with fluorescein isothiocyanate at an FITC to protein molar ratio of 3 to 1 in 0.1M sodium borate solution at a pH of 9.2 and at a temperature of 37° C. for 60 minutes. Any unreacted FITC is removed by gel filtration on Sephadex G-50. After 60 minutes at room temperature, the solution is removed and the tubes rinsed and checked under UV light. ConA bound only to glucosylated DNA in tubes containing T$_4$ DNA.

To the third set of tubes is delivered 100 μl of unlabeled ConA in PBS.Mg++ buffer. After 60 minutes at room temperature, the tubes are rinsed free of ConA with 0.2M Imidazole buffer pH 6.5.

Acid phosphatase is then added [0.005 units in 100 μl at 0.2 percent phosphatase-free BSA] and the tubes are incubated at room temperature for 30 minutes. After rinsing with 0.15M NaCl to remove any unbound enzyme, 0.1 mM paranitrophenylphosphate in 0.2M imidazole at pH 6.5 is added and incubation continued for 60 minutes at 37° C. The enzyme reaction is terminated by adding 1.0 ml of 0.5 percent sodium bicarbonate and absorbance is determined at $A_{300}$.

The resulting observed test results indicate that acid phosphatase, one component of the signalling moiety gives a positive visible color reaction, upon reaction with its chromogen, only in tubes containing "probe" T$_4$ DNA and bridging moiety, ConA, but is washed off from the tubes which contain only ConA or ConA and calf thymus DNA.

EXAMPLE 3

In an example of the method of the present invention, phage lambda DNA was employed as the analyte, glucosylated DNA as the labelled probe, ConA as the bridging entity and alkaline phosphatase with paranitrophenylphosphate as the signalling moiety. Bacteriophage lambda, obtained by heat induction of *E. coli* stain W3350 lysogenic for λC$_1$857 phage, was employed for the preparation of phage lambda DNA. In these tests, the analyte, phage lambda DNA, was immobilized on an activated glass surface according to the following procedure. After rinsing with buffer, glass tubes were coated with 100 μl of coating solution [50 percent formamide, 5X SSC, 100 μg salmon sperm DNA 0.2 percent polyvinyl pyrrolidone, 0.1 percent Triton X-100, 0.2 percent BSA and 0.05 percent SDS] at 42° C. for 90-120 minutes. The coating solution was removed and the surface was covered with 100 μl of coating solution containing phage lambda DNA.

Phage lamba DNA employed as the probe is nick translated with maltose-triose dUTP to introduce glucosyl residues into the DNA. The glucosylated minutes and rapidly cooled in ice bath immediately before use. The tubes were then incubated with probe at 42° C. for 24 hours. The solution was removed and tubes were rinsed with PBS.Mg++ buffer. As described above in example 2, ConA is added to the tubes in PBS.Mg++ buffer. After 60 minutes at room temperature the tubes are rinsed with 0.2M Imidazole buffer.

Also as described in Example 2, the signalling moiety components, acid phosphatase and paranitrophenyl phosphate, are sequentially introduced into the tubes, to generate the detectable soluble signal. In these tests, the glucosyl moiety of the DNA probe is one bridging moiety of the chemical label, and reacts with and is strongly attracted to the second bridging moiety, ConA. The results indicated that acid phosphatase was not washed off from the tubes which contained glucosylated probe, whereas tubes containing non-labelled probe did not show any enzyme activity.

EXAMPLE 4

As in the above example employing a glucosylated DNA as the labelled probe, wherein the glucosyl moiety serves as part of the chemical label, comparable results may also be achieved by employing a biotin-labeled DNA probe. When biotin is employed as a bridging moiety of the chemical label of the DNA probe, the presence of the biotin-labeled DNA probe would be elicited or detected by means of an avidin or streptavidin-linked enzyme, since avidin is strongly reactive with or strongly bonds to biotin.

For example, a biotin-labeled DNA probe would readily be detected by an enzyme complex of the character avidin-biotin-alkaline phosphatase. More specifically, the presence of the biotin-labeled DNA probe would readily be detected by contacting the hybrid containing the biotin-labeled probe with the enzyme complex avidin-biotin-alkaline phosphatase, and bringing the resulting probe and avidin-biotin-alkaline phosphatase complex into contact with a suitable substrate which, upon contact with the enzyme, would produce a soluble signal that would be readily noticed or be capable of being determined, both qualitatively and quantitatively, by photometric and/or colorimetric means. If desired, instead of an avidin-biotin-enzyme complex, there could be used an antibody to biotin for attachment to the biotin moiety of the biotin-labeled DNA probe, followed by a complex comprising anti-antibody-enzyme in the manner described above.

EXAMPLE 5

The advantages of this invention are also obtainable when the probe is immobilized on a non-porous plastic surface. When a plastic surface is employed, it is sometimes desirable to increase the effectiveness or uniformity of the fixation by pretreating the plastic surface.

Because polystyrene from various batches or sources exhibits different binding capacities, the adherence or fixing of DNA to a polystyrene surface is improved by treating the surface with an amino-substituted hydrophobic polymer or material. Previous experiments demonstrated that addition of duodecadiamine (DDA) to polystyrene resulted in an uniform binding coefficient of polystyrene plates of different batches. Another technique for improving the fixing or uniformity of the plastic surface for fixing DNA involves treatment of the surface with polylysine (PPL).

In tests involving the fixing of DNA to a plastic surface, biotinylated DNA (b-DNA) was denatured and aliquoted into Dynatech, Immulon II ™ removable wells. Samples were allowed to dry onto the plastic surface at 37° C. The amount of bound b-DNA was determined by sequential addition of goat anti-biotin antibody and rabbit anti-goat antibody complexed to the signalling moiety, alkaline phosphatase, followed by development with p-nitrophenyl phosphate in diethanolamine buffer, pH 9.6. Enzymatic activity was monitored at 405 nm utilizing the automatic Dynatech Micro ELISA Scanner. This procedure enables quantitation of the amount of bound DNA and therefore the degree of biotinylation. To increase the sensitivity of detection, a fluorogenic substrate such as 4-methylumbelliferyl-phosphate, or its analogues, with companion enzymes, may be used.

In a further example of the method, denatured adenovirus 2 DNA, the analyte, was bound to polystyrene plates as described above. After blocking with Denhardt's formamide blocking buffer, several biotinylated probes, b-adeno-2-DNA and lambda DNA were hybridized to the immobilized DNA. To one set of immobilized DNA, no probe was added. The extent of hybridization was determined by means of the antibody-enzyme reaction as described above. It was observed that only the homologous adeno-2 probe hybridized. This technique demonstrated that in vitro hybridization under these conditions is specific and can be monitored quantitatively by the method of the present invention.

Other methods for enabling fixation of single-stranded analyte to a solid support for use in the method of the present invention include the following.

EXAMPLE 6

In further tests, radioactively-labeled DNA was prepared by nick translation with [$^3$H]dATP. The labelled, non-biotinylated denatured DNA [2000 ng to 5 ng] was applied to DDA-coated polystyrene plates. The test samples or plates were not allowed to dry. After incubation at 37° C. for periods of 30 minutes, 1 hour, 2 hours, 3 hours, 4 hours, and 18 hours, samples were counted. Binding was maximal after two hours of incubation, however, 50 percent of the originally applied DNA bound regardless of the concentration, thereby indicating that there is an equilibrium between bound and unbound DNA.

In other tests, polystyrene microfilter wells were nitrated using the procedure of Filipsson and Hornby, *Biochem. J.* 120, 215 (1970). The polystyrene wells were immersed for 20 minutes in a mixture of concentrated nitric and sulfuric acid [41 percent, v/v] cooled to 0° C. The wells were then washed thoroughly with water and subsequently heated to 70° C. in a 6 percent solution of sodium dithionate in 2M potassium hydroxide. After 4 hours, the wells were washed thoroughly with 0.5M hydrochloric acid and distilled water.

To produce 6-aminohexane linked polystyrene, 6-amino-caproic acid-N-hydroxysuccinimide ester.hydrobromide [5 mg thereof dissolved in 0.2M dimethylformamide prepared by reacting 6-aminocaproic acid.hydrobromide with N-hydroxysuccinimide and dicyclohexyl carbodiimide in dimethylformamide and recrystallized from isopropyl alcohol] was added to 0.1M sodium borate [0.4 ml]. Amino-derivitized polystyrene microfilter wells filled with this solution were allowed to react at room temperature for 4 hours and then washed thoroughly with distilled water. The resulting treated wells absorbed H-labeled DNA from aqueous solution at pH less than 9.5.

An improved capability for fixing or immobilization of DNA to non-porous siliceous solid supports, such as glass and plastic, is also provided by treatment with a coating of an epoxy resin. For example, treatment of glass or polystyrene surfaces with commercially available epoxy glues, such as a solution of epoxy glue in ethanol [1 percent w/v] serves this purpose. These epoxy solutions are applied to the surfaces or wells, and the solvent, ethanol, evaporated thereupon at a temperature of 37° C., thereby providing a polyamine polymeric coating on the treated surface. These surfaces were found to absorb $^3$H-labeled DNA from aqueous solution at pH less than 9.5.

EXAMPLE 7

Yet another example of the method of the present invention, including fixing the polynucleotide analyte sequence directly to a non-porous solid support, such as a conventional microtiter well, may be performed according to the procedures outlined below.

Conventional microtiter well plates can be pre-rinsed with 1M ammonium acetate (NH$_4$OAc), in an amount of 200 μls/well. Analyte DNA would be diluted to 10–200 ng/50 ul in water or 10 mM Tris-HCl at pH 7.5 and 1 mM EDTA(TE). After boiling for 5 minutes and quick cooling in ice water, an equal volume of 2M NH$_4$OAc would be added and 50 ul of analyte DNA is added per well, giving 5–100 ng of analyte DNA per well. After open plate incubation for 2 hours at 37° C., the wells can be sealed and plates stored at 4° C. Alternatively, open plates can be incubated at 37° C. until the wells are dry, at which point the plates can be sealed, and stored at 4° C. for up to one-two months. Single-stranded analyte DNA is now fixed to the wells.

An alternative method to denature and then fix the analyte DNA to the well is to add 50 ul of DNA in TE to wells at a concentration of 10–200 ng/50 ul. After adding 25 ul at 0.9N NaOH and mixing, the plates can be incubated for 10 minutes at room temperature. After adding 25 ul of 4M NH$_4$OAc, the open plate may be incubated at 37° C. for 4 hours or until dry and the plates sealed and stored at 4° C. until ready to use.

To prepare the plates for hybridization, the wells would be rinsed twice with 0.3m NaCl, 0.03m sodium citrate (2X SSC) (200 ul/well) buffer regardless of whether the plate was dried or not. Preferably, the wells can be rinsed once with 2X SSC/1% Triton X-100 after the two 2X SSC rinses. Plates should be blotted on absorbent paper before beginning each rinse.

To hybridize the fixed analyte with a probe, the following protocol would be followed. A nick translated probe would be heat denatured and added to a hybridization solution containing 30% formamide (deionized), 2X–4X SSPE (20X SSPE=3.6M NaCl, 0.2M NaPO$_4$, pH 7.4, 0.02M EDTA) depending on the GC content of probe, 0.1% SDS, and 5.0% dextran sulfate to give a final concentration of 0.2–1.0 ug probe/ml. An alternative hybridization solution contains 30% formamide (deionized), 2X–4X SSPE, 1.0% Triton X-100, and 5.0% dextran sulfate and 0.2–1.0 ug probe/ml. 100 ul of the selected hybridization mixture is added to each well. After sealing the plates, they are incubated at 37° C. for a desired time.

The hybridization solution is poured out, or collected by aspiration for reuse if desired. The plates are rinsed twice with 2X SSC and 0.1% SDS or 2X SSC and 0.1% Triton X-100 according to whether the first or second hybridization solution identified above was employed. At this point two to four stringency rinses of SSC and detergent are preferably performed by heating the buffer to the desired temperature and adding it hot to the wells. Formamide and low SSC or SSPE can be used at 37°–40° C. to achieve the desired stringency. Following stringency washes, wells are rinsed twice with 1X SSC or 1X SSC and 0.1% Triton X-100, and the plates are now ready for detection.

Detection of the fixed hybridized analyte-probe according to the invention may employ the procedure for commercially available ELISA assays using the sensitive DETEK® 1-alkaline phosphatase or DETEK® 1-horseradish peroxidase assays (Enzo Biochem, Inc.). Beginning at the blocking procedure, the standard method is employed except that after blocking, no rinsing step is used. Complex diluted in 1X complex dilution buffer is thereafter added as taught in these commercially available assays.

As will be apparent to those skilled in the art in the light of the foregoing disclosure, many alterations, modifications and substitutions are possible in the practice of this invention, without departing from the spirit or scope thereof. Consequently, only such limitations as appear in the appended claims should be placed upon the scope of the invention.

What is claimed is:

1. A method for detecting a polynucleotide sequence which comprises:
    fixing said polynucleotide sequence to a solid support which comprises or is contained within a transparent or translucent, non-porous system, such that a single-strand of the polynucleotide is capable of hybridizing to complementary nucleic acid sequences;
    forming an entity comprising said polynucleotide sequence hybridized to a polynucleotide or oligonucleotide probe, said probe having attached thereto a chemical label further comprising a signalling moiety capable of generating a soluble signal; and
    generating and detecting said soluble signal.

2. The method according to claim 1, wherein said detecting step comprises spectrophotometric techniques.

3. The method according to claim 1, wherein said soluble signal is selected from the group consisting of a colored product, a chemiluminescent product and a fluorescent product.

4. The method according to claim 1, wherein said signalling moiety is selected from the group consisting of an enzyme, a chelating agent and a co-enzyme.

5. The method according to claim 1, wherein said solid support is selected from the group consisting of glass, plastic, polystyrene, polyethylene, dextran and polypropylene.

6. The method according to claim 1, wherein said polynucleotide sequence is directly fixed to said solid support.

7. The method according to claim 6, wherein said polynucleotide sequence is fixed to said solid support in single stranded form.

8. The method according to claim 1, wherein said signalling moiety is attached to said polynucleotide or oligonucleotide probe through the formation of a complex.

9. The method according to claim 8, wherein said complex is selected from the group consisting of biotin and avidin, biotin and streptavidin, and a sugar and a lectin.

10. The method according to claim 1, wherein said forming step further comprises washing to remove said polynucleotide or oligonucleotide probes that do not form said entity.

11. The method according to claim 10, wherein said forming step further comprises attaching said signalling moiety to said polynucleotide or oligonucleotide probe after said washing step.

12. The method according to claim 11, which further comprises separating free signalling moieties from said attached signalling moieties.

13. The method according to claim 1, wherein said detecting step further comprises generating said soluble signal in a device capable of transmitting light therethrough for the detection of said soluble signal by spectrophotometric techniques.

14. The method according to claim 13, wherein said device is selected from the group consisting of a well, a tube, a cuvette and an apparatus which comprises a plurality of said wells, tubes or cuvettes.

15. The method according to claim 13, wherein said soluble signal is selected from the group consisting of a colored product, a chemiluminescent product, and a fluorescent product.

16. The method according to claim 13, wherein said solid support and said device are composed of the same materials.

17. A device for detecting a polynucleotide sequence according to the method of claim 1, which device comprises a solid support, having said polynucleotide sequence fixed thereto in hybridizable form.

18. A kit for detecting a polynucleotide sequence, which comprises the device of claim 17 in packaged combination with a container of an oligonucleotide or polynucleotide probe, having covalently attached thereto a chemical label comprising a signalling moiety capable of generating a soluble signal.

19. The kit of claim 18, wherein said soluble signal is a colored product or a fluorescent product.

20. The method according to claim 1 wherein part of the solid support is modified to facilitate fixing of the polynucleotide sequence to the solid support by the sequential steps of:
    (a) heating or boiling the solid support in dilute nitric acid for about 45 minutes;
    (b) washing or rinsing the solid support with distilled water;
    (c) drying the solid support at about 115° C., for about 24 hours;
    (d) incubating the solid support in contact with 10% gamma-aminopropyltriethoxysilane for about two to three hours at about 45° C.;
    (e) washing with water; and
    (f) drying overnight at a temperature of about 100° C.

21. The method according to claim 1 wherein part of the solid support is modified to facilitate fixation of the polynucleotide sequence to the solid support by treating the solid support with a coating of an epoxy resin.

22. The method according to claim 21 wherein part of the solid support is modified to facilitate fixation of the polynucleotide sequence to the solid support by treating the support with the epoxy resin by the following sequential steps;
  (a) applying an epoxy glue in solution with ethanol to the solid support; and,
  (b) evaporating the ethanol by heating to a temperature of about 37° C. to provide a polyamine polymeric coating on the solid support.

23. The method according to claim 1 wherein said polynucleotide sequence is fixed to said solid support in double-stranded form, and denatured into single-stranded form prior to the hybridization step.

24. The method according to claim 1 wherein said polynucleotide sequence in double-stranded form is denatured, and fixed to said solid support in single-stranded form prior to the hybridization step.

25. The method according to claim 1 wherein said polynucleotide sequence to be detected is in single-stranded form and is indirectly bound to said solid support by sandwich hybridization.

26. The method according to claim 1 wherein a cell or cellular material is directly fixed to said solid support, and polynucleotide sequences within said material are hybridized to polynucleotide or oligonucleotide probes in situ.

27. The method according to claim 1 wherein said signalling moiety is a chemiluminescent agent.

* * * * *

UNITED STATES PATENT AND TRADEMARK OFFICE
Certificate

Patent No. 4,994,373                                                           Patented: February 19, 1991

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jannis G. Stavrianopolous, New York, NY (US); Dollie Kirtikar, Elmhurst, NY (US); Kenneth H. Johnston, New York, NY (US); Barbara E. Thalenfeld, New York, NY (US); and Elazar Rabbani, New York, NY (US).

Signed and Sealed this Seventeenth Day of April 2007.

WILLIAM R. DIXON, JR.
*Special Program Examiner*
Technology Center 1600